(12) United States Patent
Basu et al.

(10) Patent No.: US 6,862,335 B2
(45) Date of Patent: Mar. 1, 2005

(54) SYSTEM AND METHOD FOR ITERATIVE RECONSTRUCTION OF CONE BEAM TOMOGRAPHIC IMAGES

(75) Inventors: Samit Basu, Niskayuna, NY (US); Bruno De Man, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 52 days.

(21) Appl. No.: 10/609,178

(22) Filed: Jun. 27, 2003

(65) Prior Publication Data

US 2004/0264625 A1 Dec. 30, 2004

(51) Int. Cl.⁷ .............................................. A61B 6/03
(52) U.S. Cl. .......................................... 378/4; 378/901
(58) Field of Search ............................ 378/4, 8, 15, 19, 378/901

(56) References Cited

U.S. PATENT DOCUMENTS

| | | | |
|---|---|---|---|
| 5,270,926 A | 12/1993 | Tam et al. | 364/413.19 |
| 5,384,573 A * | 1/1995 | Turpin | 342/179 |
| 5,736,958 A * | 4/1998 | Turpin | 342/179 |
| 5,751,243 A * | 5/1998 | Turpin | 342/179 |
| 5,909,476 A | 6/1999 | Cheng et al. | 378/4 |
| 6,510,241 B1 | 1/2003 | Vaillant et al. | 382/154 |
| 2004/0062447 A1 * | 4/2004 | Suarez et al. | 382/240 |

OTHER PUBLICATIONS

L.A. Feldkamp, L.C. Davis, J.W. Kress, et al, "Practical Cone–Beam Algorithm", Journal of the Optical Society of America A, 1:612–19, Jun. 1984.

* cited by examiner

Primary Examiner—David V Bruce
(74) Attorney, Agent, or Firm—Fletcher Yoder

(57) ABSTRACT

A method for refining image data from measured projection data acquired from a computed tomographic scanner is provided. Initially, measured projection data from the computed tomographic scanner is received. The measured projection data is reconstructed to generate initial reconstructed image data. The initial reconstructed image data is partitioned into a plurality of volumes based on image data quality, to generate partitioned reconstructed image data. The plurality of volumes comprise a good image data quality volume and a poor image data quality volume. Then the image data quality of the partitioned reconstructed image data is refined to generate an improved reconstructed image data.

39 Claims, 7 Drawing Sheets

SYSTEM AND METHOD FOR ITERATIVE RECONSTRUCTION OF CONE BEAM TOMOGRAPHIC IMAGES

BACKGROUND OF THE INVENTION

The present invention generally relates to the field of image reconstruction in Computed Tomography (CT) imaging systems and more particularly to a system and method for iterative reconstruction of cone beam tomographic images.

CT scanners operate by projecting fan shaped or cone shaped X-ray beams through an object. The X-ray beams are generated by an X-ray source, and are generally collimated prior to passing through the object being scanned. The attenuated beams are then detected by a set of detector elements. The detector element produces a signal based on the intensity of the attenuated X-ray beams, and the signals are processed to produce projections. By using reconstruction techniques, such as filtered backprojection, useful images are formed from these projections.

A computer is able to process and reconstruct images of the portions of the object responsible for the radiation attenuation. As will be appreciated by those skilled in the art, these images are computed by processing a series of angularly displaced projection images. This data is then reconstructed to produce the reconstructed image, which is typically displayed on a cathode ray tube, and may be printed or reproduced on film.

As CT scanners are developed with larger and larger detectors, they begin to encounter problems with artifacts in the reconstructions that arise due to the cone angle of the scanner. An increase in the cone angle beyond a certain limit, can result in a degradation of the image quality produced by the scanner.

One technique that has been employed to address cone beam artifacts is through the use of iterative reconstruction techniques. However, iterative reconstruction techniques require enormous amounts of computation and are not useful in practice unless the volume to be reconstructed is small. A technique for obtaining improved image quality without the high computational burden associated with it is therefore desired.

BRIEF DESCRIPTION OF THE INVENTION

In one embodiment, a method for refining image data from measured projection data acquired from a computed tomographic scanner is provided. Initially, measured projection data from the computed tomographic scanner is received. This measured projection data is reconstructed to generate initial reconstructed image data. The initial reconstructed image data is partitioned into a plurality of regions based on expected image data quality, to generate partitioned reconstructed image data. The plurality of regions in the initial reconstructed image data comprise a good image data quality volume and a poor image data quality volume. Then the image data quality of the partitioned reconstructed image data is refined to generate an improved reconstructed image data.

In a second embodiment, a computed tomography system, method and computer readable medium for refining image data is provided. The computed tomography system comprises an X-ray source configured to project a plurality of X-ray beams through the object and a detector configured to produce a plurality of electrical signals corresponding to the X-ray beams. The computed tomography system further comprises a processor configured to process the electrical signals to generate a plurality of projection measurements. The processor is configured to perform calculations on the projection measurements to generate reconstruction volume data. The calculations comprise partitioning the reconstruction volume data into a plurality of regions based on image data quality.

In a third embodiment, a method, system and computer readable medium of refining image data of an object based on a reconstruction volume generated by initial reconstructed image data of a computed tomographic scanner is provided. The reconstruction volume is partitioned into a first, second and third volume. The first volume comprises radiation paths from a central portion of a radiation beam generated by the computed tomographic scanner that intersect radiation paths from diametrically opposed source positions. The second volume comprises radiation paths from an outer portion of a radiation beam generated by the computed tomographic scanner that intersect radiation paths from diametrically opposed source positions. The third volume comprises non-intersecting radiation paths of a radiation beam generated by the computed tomographic scanner. The voxel values for the first volume, the second volume, and the third volume are computed. The voxel values for the voxels of the third volume are then iteratively updated to generate a refined image data of the object.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
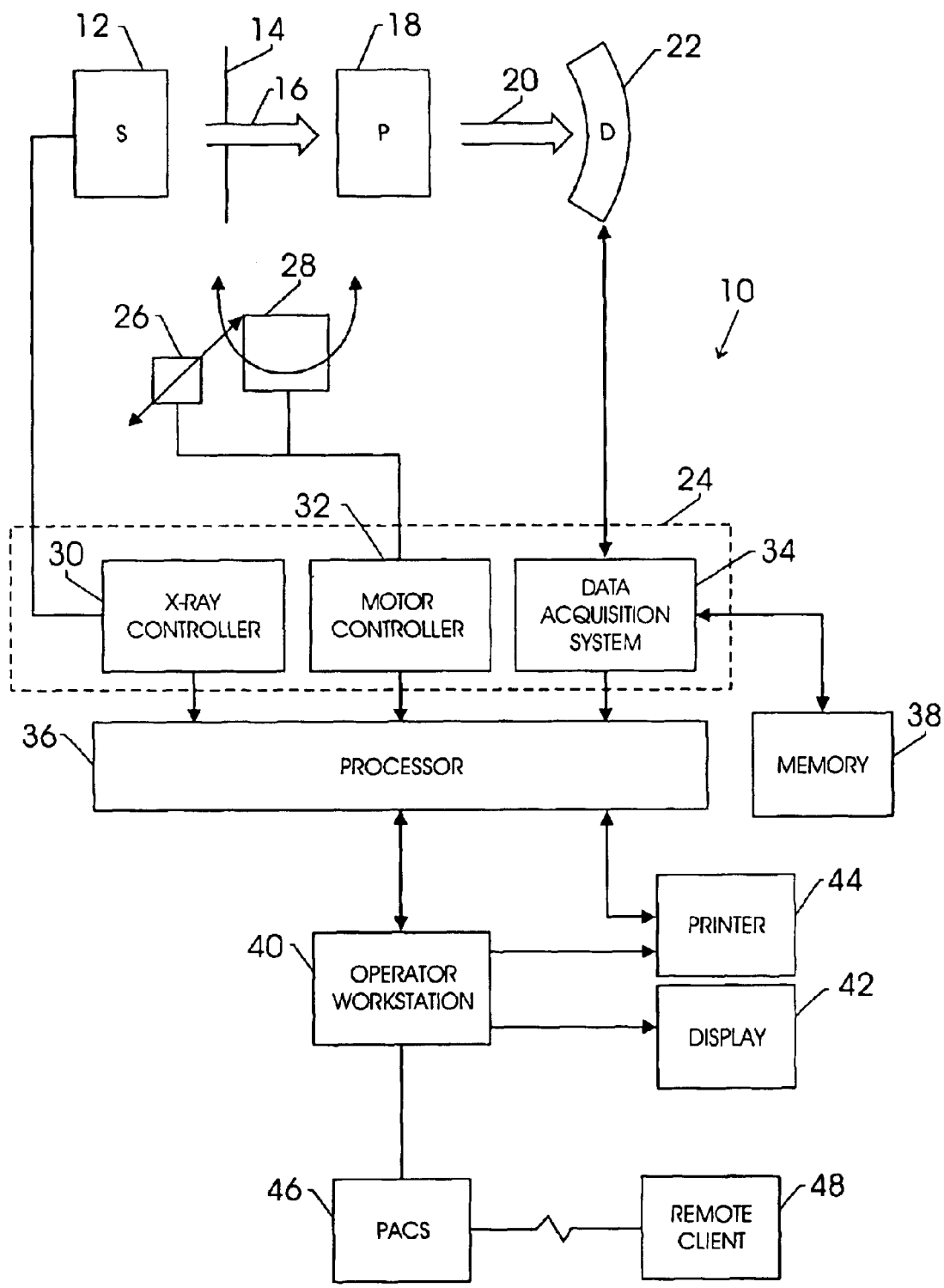
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which an object 18 is positioned. A portion of the radiation 20 passes through or around the object and impacts a detector array, represented generally at reference numeral 22. Detector elements of the array produce electrical signals that represent the intensity of the incident X-ray beam. These signals are acquired and processed to reconstruct an image of the features within the object.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the object 18. It should be noted that the rotational subsystem 28 might include a gantry. Thus, the system controller 24 may be utilized to operate the gantry. The linear positioning subsystem 26 enables the object 18, or more specifically a table, to be displaced linearly. Thus, the table may be linearly moved within the gantry to generate images of particular areas of the object 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor 36.

The processor 36 is typically coupled to the system controller 24. The data collected by the data acquisition system 34 may be transmitted to the processor 36 and moreover, to a memory 38. It should be understood that any type of memory to store a large amount of data-might be utilized by such an exemplary system 10. Moreover, the memory 38 may be located at this acquisition system or may include remote components for storing data, processing parameters, and routines described below. Also the processor 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from processor 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the processor 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image and to the image data.

It should be further noted that the processor 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
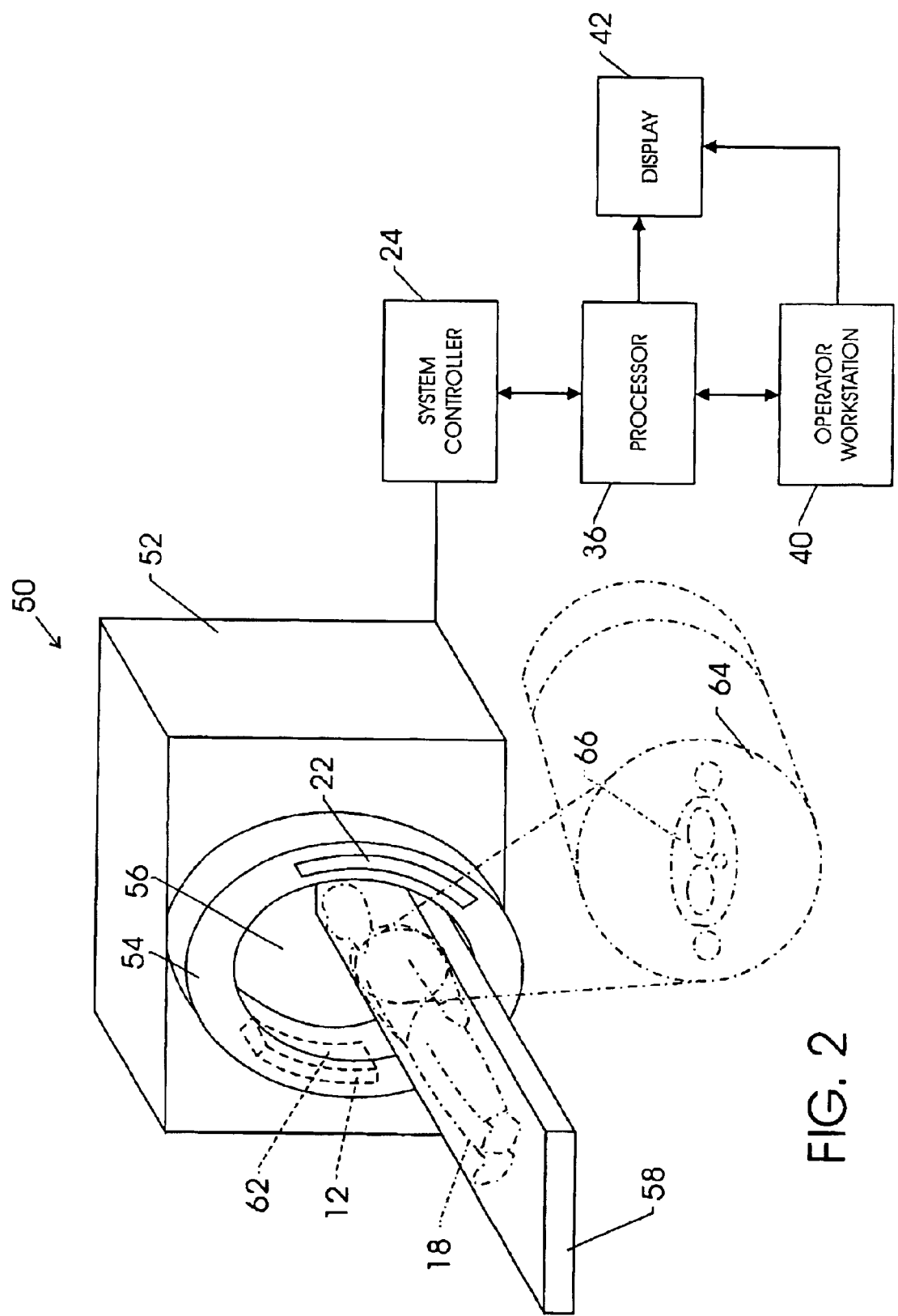
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MDCT) system that offers a wide array of axial coverage, high gantry rotational speed, and high spatial resolution. The CT scanning system 50 is illustrated with a frame 52 and a gantry 54 that has an aperture 56. The aperture 56 may typically be 50 cm in diameter. Further, a table 58 is illustrated positioned in the aperture 56 of the frame 52 and the gantry 54. Additionally, the table 58 is configured to be displaced linearly by the linear positioning subsystem 26 (see FIG. 1). The gantry 54 is illustrated with the source of radiation 12, typically an X-ray tube that emits X-ray radiation from a focal point 62. In typical operation, X-ray source 12 projects an X-ray beam from the focal point 62 toward detector array 22. The detector 22 is generally formed by a plurality of detector elements, which sense the X-rays that pass through and around an object of interest. Each detector element produces an electrical signal that represents the intensity of the X-ray beam at the position of the element at the time the beam strikes the detector. Furthermore, the gantry 54 is rotated around the object of interest so that a plurality of radiographic views may be collected by the processor 36. Thus, an image or slice is computed which may incorporate, in certain modes, less or more than 360 degrees of projection data, to formulate an image. The image is collimated to desired dimensions, using either lead shutters in front of the X-ray source 12 and different detector apertures. The collimator 14 (see FIG. 1) typically defines the size and shape of the X-ray beam that emerges from the X-ray source 12. Thus, as the X-ray source 12 and the detector 22 rotate, the detector 22 collects data of the attenuated X-ray beams.

Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area. As mentioned above, the processor 36 is typically used to control the entire CT system 10. The main processor that controls the operation of the system may be adapted to control features enabled by the system controller 24. Further, the operator workstation 40 is coupled to the processor 36 as well as to a display, so that the reconstructed image may be viewed. Alternatively, some or all of the processing described herein may be performed remotely by additional computing resources based upon raw or partially processed image data.

While in the present discussion reference is made to a CT scanning system in which a source and detector rotate on a gantry arrangement, it should be borne in mind that the present technique is not limited to data collected on any particular type of scanner. For example, the technique may be applied to data collected via a scanner in which an X-ray source and a detector are effectively stationary and an object is rotated, or in which the detector is stationary but an X-ray source rotates. Further, the data could originate in a scanner in which both the X-ray source and detector are stationary, as where the X-ray source is distributed and can generate X-rays at different locations. Similarly, while generally circular scan geometries are discussed, other geometries may be envisioned as well. More generally, for any source trajectory and for any geometry where a region of relatively good image quality data and a region of relatively poor image quality data can be identified, techniques such as those described herein may be employed to improve the quality of the reconstructed image in a computationally efficient manner.

Once reconstructed, the image produced by the system of FIGS. 1 and 2 reveals internal features of an object. As illustrated generally in FIG. 2, the image 64 may be displayed to show these features, such as indicated at reference numeral 66 in FIG. 2.

Figure 3:
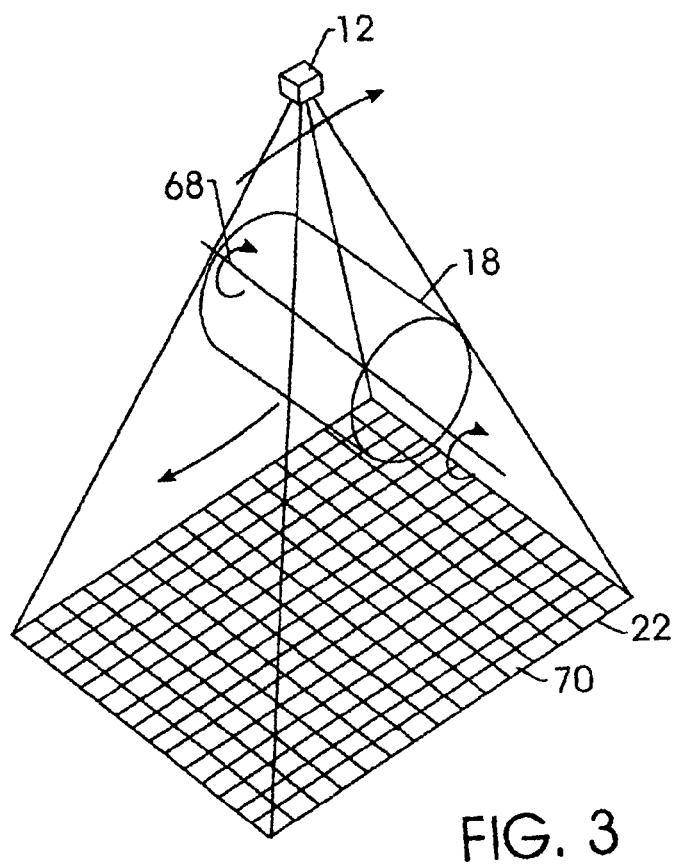
FIG. 3 is an illustration of a typical data acquisition configuration employing cone beam geometry.

FIG. 3 is an illustration of a typical data acquisition configuration employing circular cone beam geometry. As shown in FIG. 3, an object 18 is positioned within a field of view between a cone beam X-ray point source 12 and a two dimensional detector array 22, which provides measured projection data 70. An axis of rotation 68 passes through the field of view and the object 18. For scanning the object 18 at a plurality of angular positions, the source 12 moves relative to the object 18 and the field of view along a circular scanning trajectory, while the detector 22 remains fixed with respect to the source. As a result of the relative movement of the cone beam source 12 to different source positions, along a scan path, the detector 22 acquires corresponding sets of cone beam projection data 70 to reconstruct the image of the object 18. Each set of cone beam data is representative of X-ray attenuation caused by the object at different source positions. The primary advantages of cone-beam geometry include reduced data acquisition time, improved image resolution, and optimized photon utilization.

Figure 4:
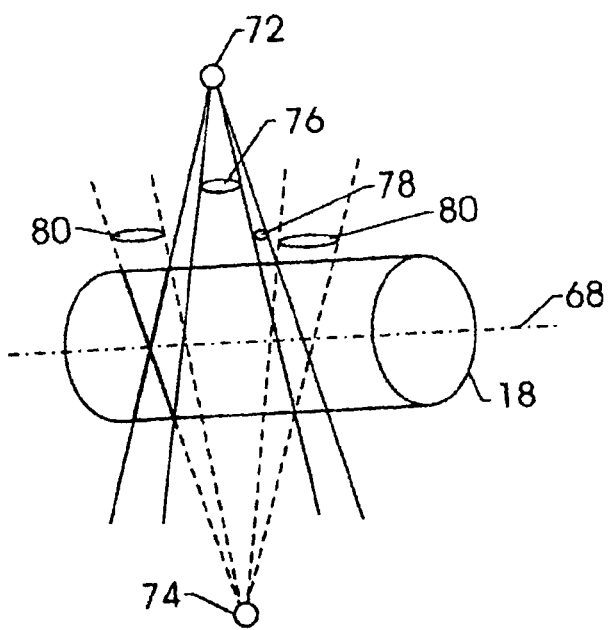
FIG. 4 is an illustration of the cone beam geometry of FIG. 3 at two diametrically opposed X-ray source positions.

FIG. 4 is an illustration of a cross section of the circular cone beam geometry of FIG. 3 through two diametrically opposed X-ray source positions 72 and 74. Reference numeral 76 indicates radiation paths from a central portion of a radiation beam generated by the computed tomographic scanner from the diametrically opposed source positions 72 and 74 that intersect one another. Reference numeral 78 indicates outlying radiation paths that also traverse a second volume. Reference numeral 80 indicates an extension of the same radiation paths in a volume that is not traversed by paths from an opposed source position. As mentioned above, while FIG. 4 illustrates a particular case of interest in which a circular scan geometry results in data of good and poor quality in the two volumes identified, the present technique is not to be limited to any particular scan geometry or to any particular underlying radiation trajectory pattern that results in the different quality data.

Figure 5:
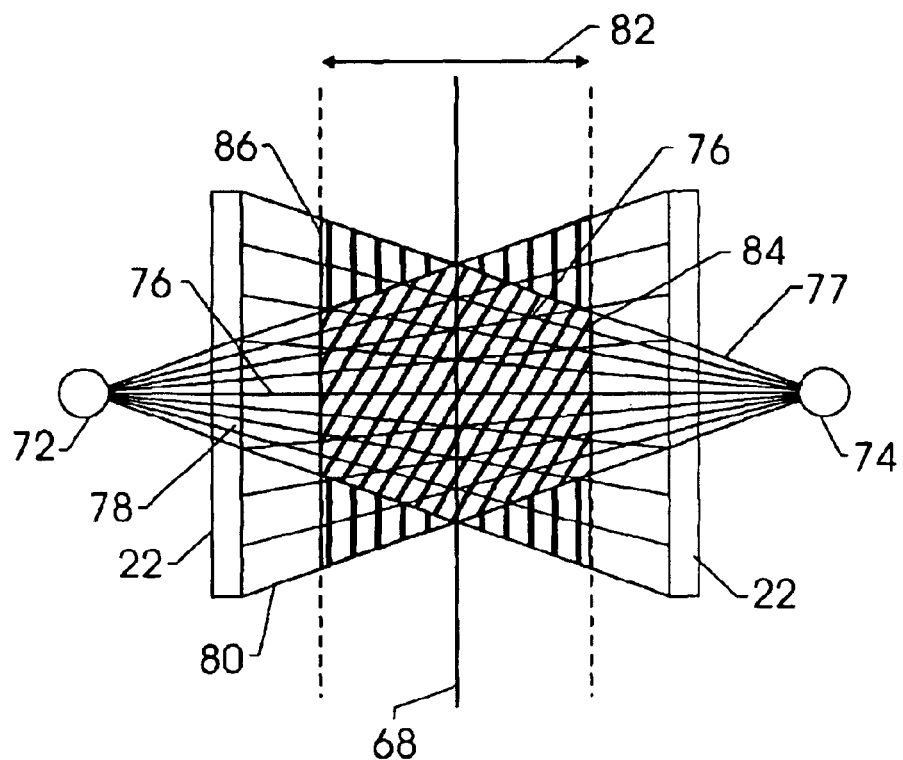
FIG. 5 is an illustration of the geometry of a reconstruction volume defined by the cone beam geometry of FIG. 4.

FIG. 5 is an illustration of the geometry of a reconstruction volume generated by the cone beam geometry of FIG. 4. The reconstruction volume comprises an array of volume elements or voxels, created from the measured projection data 70. Reference numeral 82 indicates the field of view.

Various cone beam analytical reconstruction techniques are available and may be used in the present invention for generating a reconstruction volume comprising an initial reconstructed image data. In a present embodiment, a cone beam filtered backprojection algorithm is used to generate the initial reconstructed image data. In a more specific embodiment, the FeldKamp Davis Kreiss (FDK) technique is used, which is an approximate reconstruction algorithm for circular cone-beam geometry.

As will be appreciated by those skilled in the art, the FDK technique comprises the steps of weighting, filtering and backprojection of data for each projection measurement over the reconstruction volume. The weighting of the projection data is performed with a point-by-point multiplication by a pre-calculated 2D array. The filtering or convolution step filters the image data to decorrelate them and may be carried out as a series of one-dimensional convolutions. In the backprojection step, the projection measurements are added to all picture elements in an image along the lines of the original projection paths.

Referring again to FIG. 5, the reconstruction volume generated by the FDK technique is partitioned into a plurality of regions or volumes based on image data quality. The plurality of regions comprise what may be referred to as a good image data quality volume 84 and a poor image data quality volume 86. As shown in FIG. 5, reference numerals 72 and 74 indicate two diametrically opposed source positions. As will be appreciated by those skilled in the art, as used herein, the terms good and poor image data quality relate to image data quality reliability assumptions (for each region or volume in the partitioned reconstruction volume) made by the reconstruction technique, wherein the image data quality reliability is generally assumed to be poor in the region comprising non-intersecting radiation paths.

As will be appreciated by those skilled in the art, the image data quality is often related to the completeness of the available projection data corresponding to that given region. In the instance of a circular scan, the good image quality region is typically the set of voxels that are irradiated during the full extent of the circle scan, while the poor image quality region is typically the set of voxels that are irradiated during less than the full extent of the circle scan.

In the present technique, as described in greater detail below, the good image data quality volume comprises voxels that are traversed by radiation paths or rays from both diametrically opposed source locations. The poor image data quality volume comprises voxels that are traversed by radiation paths from only one of the opposed locations. In other terms, based upon these regions, two sets of radiation paths or rays may be identified. A first set includes those rays that cross only the good data quality volume, and a second set includes those rays that traverse both the good and poor data quality volumes. Based upon these two sets of radiation paths, two portions of the good data quality volume may, in turn, be identified. A first portion comprises voxels that are traversed only by radiation paths from opposed source locations that cross only the good image quality volume. The second portion comprises voxels that are traversed by radiation paths that also traverse the poor image data quality volume. As described below, after computing values for voxels of both of these portions and for voxels of the poor image data quality volume, the values of the good image quality regions are not altered or updated. However, the computed values of the voxels for the second portion of the good image data quality volume are used to iteratively adjust the computed values for the poor image data quality volume.

Figure 6:
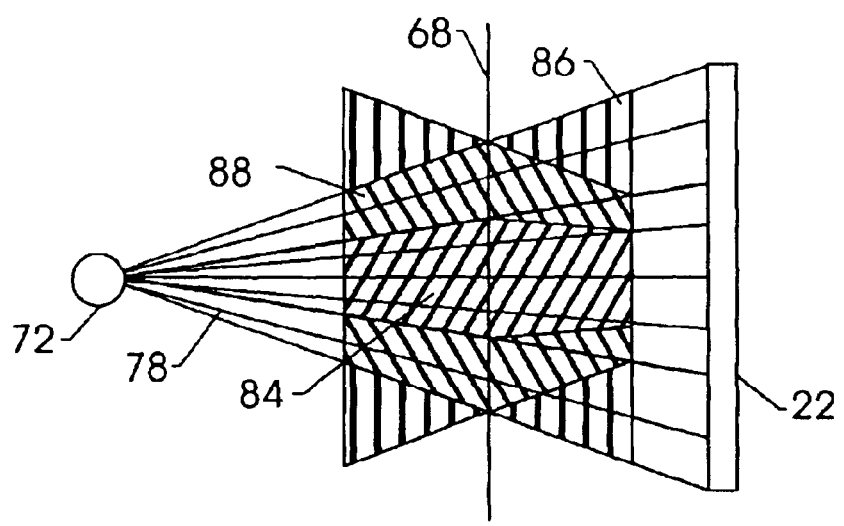
FIG. 6 is an illustration of analytically partitioned portions of the reconstruction volume of FIG. 5.

This analysis of the volumes and portions is illustrated in FIGS. 4, 5 and 6. Referring to FIGS. 4, 5 and 6, the good image data quality volume 84, again, comprises radiation paths from a central portion of a radiation beam 76 generated by the computed tomographic scanner, when considering the circular scan geometry depicted, as indicated in FIG. 4. FIG. 6 illustrates the two portions of the good image data quality volume, as discussed above. The second portion of this volume, indicated by reference numberal 88, comprises radiation paths from an outer portion of a radiation beam 78 generated by the computed tomographic scanner, when considering the circular scan geometry. As shown in FIG. 5, the poor image data quality volume 86 lies on either side of the good image data quality volume in the geometry shown. In this application, outer paths of the radiation beam, indicated by reference numeral 78 comprise radiation paths through the good image data quality volume 84 that also pass through the poor image data quality volume 86 of the reconstruction volume.

As described more fully below, the present technique provides for performing a first pass analytical reconstruction on both the first, good image data quality, and second, poor image data quality volumes. The voxel values for the good image quality volume are then retained and are not iteratively updated. However, the values for the voxels of the poor image data quality volume are iteratively adjusted. That is, in the present embodiment, reprojections through the poor image data quality volume are re-computed at every iteration. Reprojections through the second portion 88 of the good image quality data are computed only once. Both sets of reprojections are then combined, and the combination is compared to the measured values. An error measurement is calculated based upon the comparison. The poor image data quality volume is then updated based on the error. The process proceeds by reducing the error until the desired image quality (i.e. match between the calculated values and the measured values) is obtained, or until some other stopping criterion is met.

Figure 7:
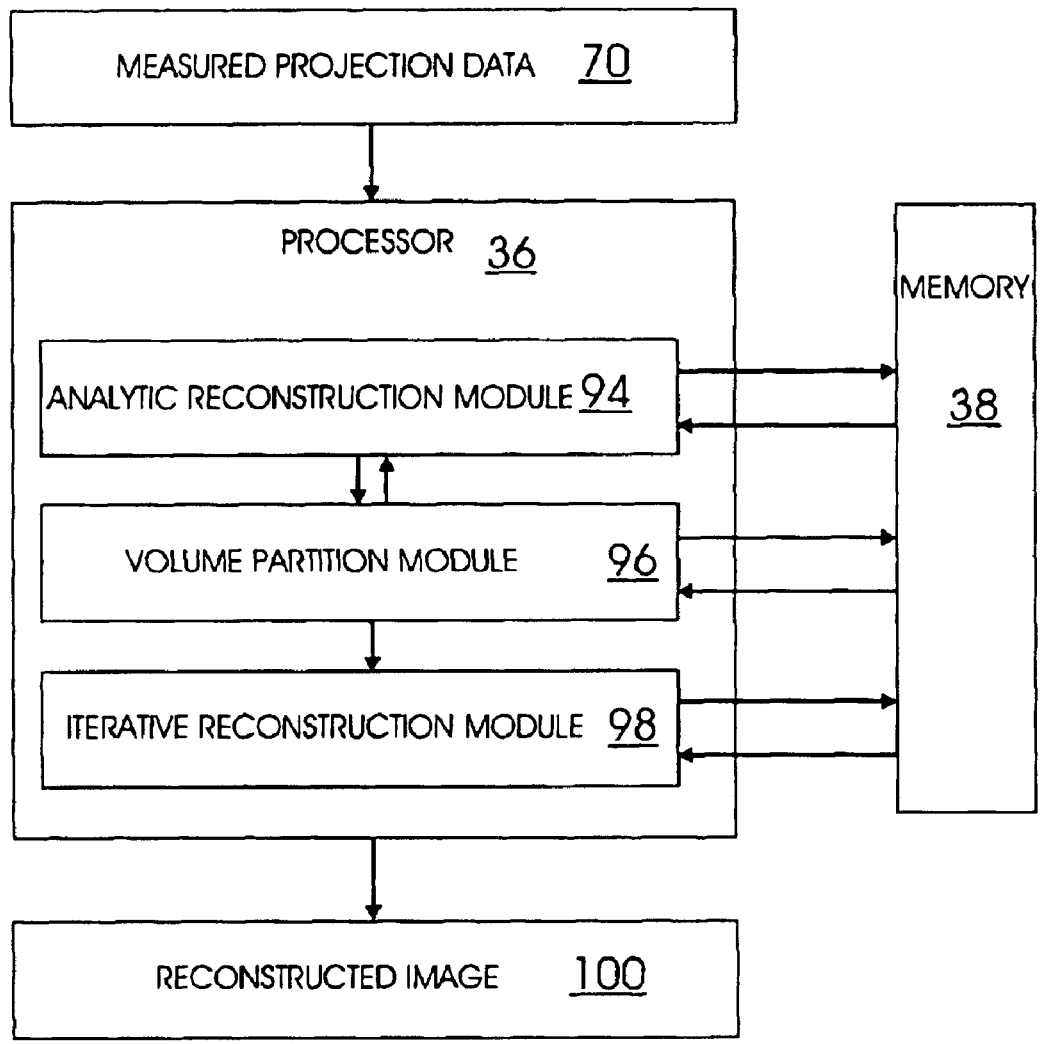
FIG. 7 is a block diagram illustrating the modules used by the processor of the CT system of FIG. 1 for refining image data of an object based on the reconstruction volume defined in FIG. 5.

FIG. 7 illustrates the modules used by the processor 36 of the CT system of FIG. 1 for partitioning the reconstruction volume into a plurality of regions and refining image data of an object based on the reconstruction volume. FIG. 7 is a block diagram 92 illustrating the modules used by the processor 36 of the CT system 10 of FIG. 1 for refining image data of an object based on the reconstruction volume shown in FIG. 5 and discussed above. The processor 36 comprises an analytic reconstruction module 94, a volume partition module 96, and an iterative reconstruction module 98. The processor 36 receives measured projection data 70 from the CT system 10. The processor 36 further processes electrical signals corresponding to radiation beams generated by the CT system 10 to generate projection measurements 70. The processing comprises performing calculations on the projection measurements 70 to generate reconstruction volume data. The above functions of the processor 36 are described in detail below.

The analytic reconstruction module 94 reconstructs the measured projection data 70 to generate initial reconstructed image data. As mentioned above, the FDK technique, which is an approximate reconstruction algorithm for circular cone-beam geometry is used in a present embodiment to create the initial reconstructed image data.

The volume partition module 96 partitions the reconstruction into a plurality of regions or volumes. The volume is divided into a first region of voxels that are to be updated through iteration (volume I), and a second volume that is not to be updated through iteration (volume II). The second volume (volume II) is further partitioned into a volume (IIA) of voxels for which radiation paths through these voxels also pass through volume I, and a volume (IIB) of voxels for which radiation paths through these voxels do not pass through volume I. In the particular instance of a circular cone beam scan, the region to be updated (volume I) consists of a poor image data quality region 86 in FIG. 6. The region (volume IIA) that is not to be updated but for which radiation paths exist that pass through volume I is the good image data quality region 88 in FIG. 6. The region (volume IIB) that is not to be updated and for which no radiation paths exists that pass through volume I is the good image data quality region 84 in FIG. 6. With this general approach in mind, the processes are described below in terms of the regions 84, 86 and 88 in FIG. 6. Those skilled in the art will recognize that FIG. 6 represents only one choice of Volumes I, IIA and IIB, as selected for a circular cone beam acquisition and partitioned based on the assumptions of poor and good image quality.

Figure 8:
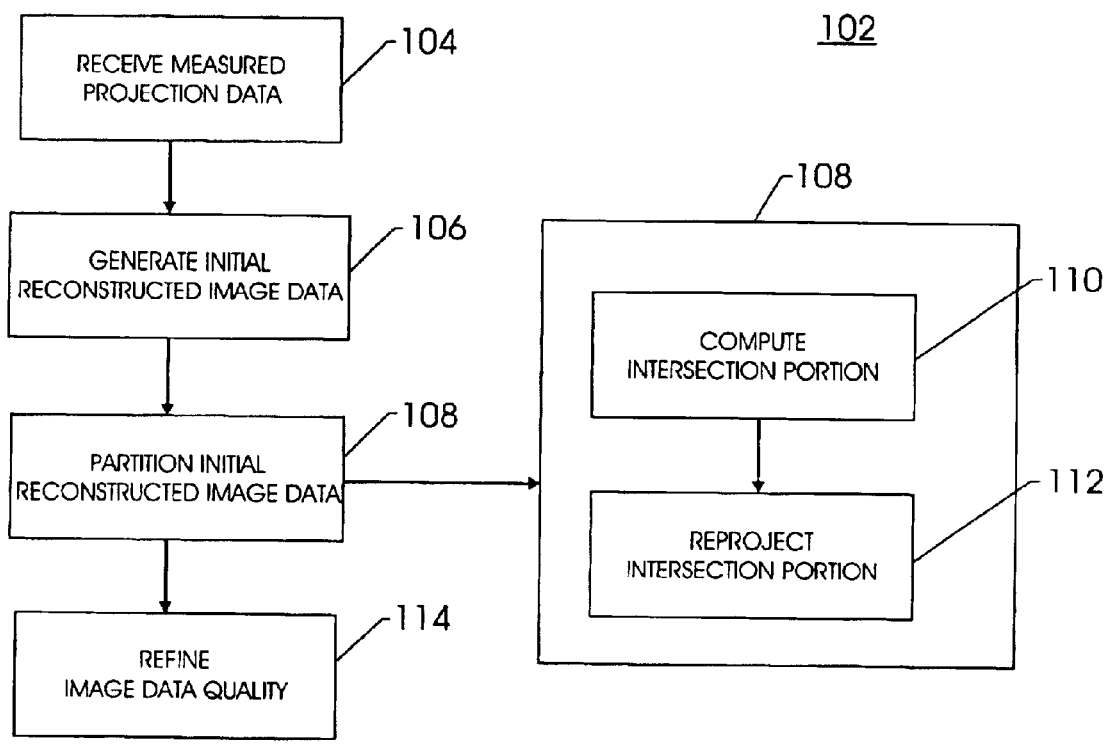
FIG. 8 is an exemplary illustration of the steps performed by the modules of FIG. 7 for refining image data of the object based on the reconstruction volume.

The iterative reconstruction module 98 iteratively computes voxel values for voxels of volume 86 to generate refined reconstructed image data 100 of the object. In a present embodiment, the iterative reconstruction module 98 uses the Maximum Likelihood Transmission Reconstruction (MLTR) technique, which is an iterative reconstruction algorithm to compute voxel values for voxels of the second volume. FIG. 8 describes in further detail, the interactions of the modules of FIG. 7 for refining image data of the object.

FIG. 8 is an exemplary illustration of the steps performed by the modules of FIG. 7 for refining image data of the object based on the reconstruction volume. The process 102 of FIG. 8 starts with receiving measured projection data from the CT system 10 in step 104. In the present embodiment, the measured projection data comprises cone beam projections.

Next, in step 106, initial reconstructed image data is generated. As mentioned above, the FDK technique, which is an approximate reconstruction algorithm for circular cone-beam geometry is used in the present embodiment to generate the initial reconstructed image data. In step 108, the reconstruction volume of the initial reconstructed image data generated in step 106 is partitioned. The partitioning comprises segmenting the reconstruction volume of the initial reconstructed image data into volumes of good and poor image data quality, wherein the good and poor image data quality volumes are determined by the geometry of the CT scanner as depicted in FIG. 5. The partitioning step 108, further comprises computing identifying a portion 88 of the good image data quality volume 84 (described above) and the poor image data quality volume 86 in step 110. The portion 88, again, corresponds to those voxels of the good data quality volume 84 through which radiation paths pass, that also pass through the poor image data quality volume 86. Voxel values of all of these volumes can be precomputed for a given cone beam geometry. In step 112 the portion 88 computed in step 110 is reprojected to generate projection data for voxels of that portion. In a present embodiment, the process of step 112 is performed only once since the good image data quality volume, and thus the corresponding projection data, does not need to be subsequently updated. It may be noted that, by partitioning the reconstruction volume into regions based on image data quality, the number of computations that would be performed in other techniques to refine both the voxel values of the good image data quality volume and the poor image data quality volume is significantly reduced. Then, the process passes to step 114, described in further detail in FIG. 9.

Figure 9:
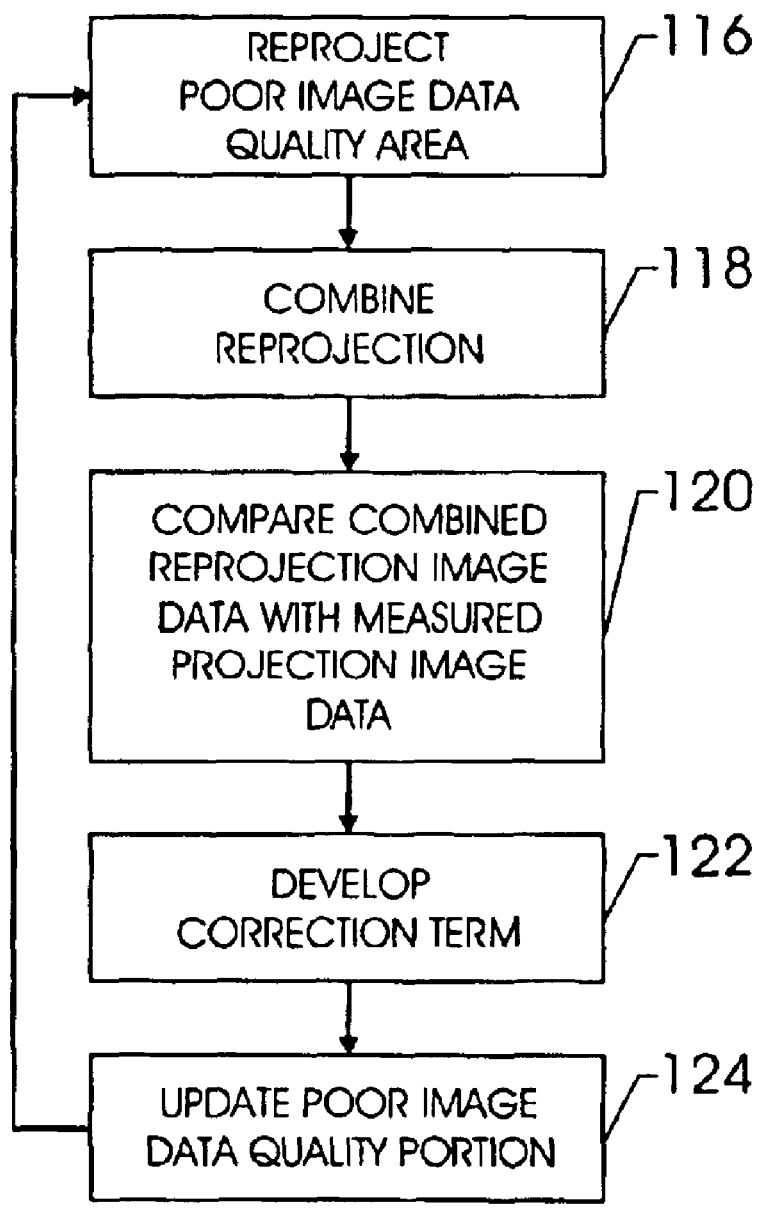
FIG. 9 is an exemplary illustration of the "refine image data quality" step of FIG. 8.

FIG. 9 is an exemplary embodiment of the "refine image data quality" step 114 of FIG. 8. In step 116, the poor image data quality volume 86 of the reconstruction volume is reprojected. The reprojection comprises computing line integrals through the volume that simulate the attenuation along X-ray beam paths through the object. Each iteration incrementally improves the image data quality of the reconstruction volume in the region of poor image data quality. The iterative update process starts by combining the reprojection of the poor image data quality volume with the reprojection of the good data quality volume. The combined reprojections are then compared with the measurements, and voxel values of the poor image data quality volume are updated so as to better match these measurements. It may be noted here, that the second portion 88 (see FIG. 6) reprojection image data (one time computation) as described in step 112, is made use of in each iteration of the iterative update process.

Various iterative reconstruction techniques are available and may be used in the present application for iteratively updating the poor image data quality volume to obtain a desired image quality. As will be appreciated by those skilled in the art a typical iterative reconstruction algorithm comprises defining an optimization criterion or cost function and optimizing the criterion in each iterative update step. A typical iterative reconstruction algorithm starts with assumed or simulated image data, computes projections from the image data, compares the computed projections with the original measurements and updates the image data based on the difference between the calculated projections and the actual measurements. As mentioned above, the Maximum Likelihood Transmission Reconstruction (MLTR) technique, which is an iterative reconstruction algorithm, is used. As will be appreciated by those skilled in the art, the MLTR technique is based on maximizing the probability of generating a required image data from an original set of projection measurements.

Referring again to FIG. 9, in step 120, the combined reprojection image data 118 is compared with the measured projection data 70 to generate a correction term for the poor image data quality volume of the reconstructed image. In step 122, the correction term is developed. The correction term is a measure of the desired image data quality to be attained by the poor image data quality volume of the reconstructed image. In one embodiment of the invention, the correction term is based on the difference or ratio between the combined reprojection data and the measured projection data, which is backprojected to the image volume. In step 124, voxel values of the poor image data quality volume are updated. The update continues until the correction step computed in step 122 attains a pre-determined value. In one embodiment of the invention, the pre-determined value is a stopping criterion. The stopping criterion is either based on a pre-defined number of iterations, a pre-defined number of image data updates or a pre-defined cost function.

The embodiments described above have several advantages, including the ability to obtain improved image data quality of an object through iterative image improvement of a cone beam filtered backprojection reconstruction technique only in the volume of poor image data quality, thereby reducing the high computational burden associated with iterative reconstruction techniques. In terms of volumes as described above, the computations of voxels for the first, or good image data quality volume, including the first and second portions of that volume are one time computations. The computations are repeated only in the part of the reconstruction volume corresponding to radiation paths that do not intersect (i.e. second or poor image data quality volume). Since there are significantly fewer voxels in the second volume the efficiency of the iterative reconstruction technique is significantly improved.

While the invention may be susceptible to various modifications and alternative forms, specific embodiments have been shown by way of example in the drawings and have been described in detail herein. However, it should be understood that the invention is not intended to be limited to the particular forms disclosed. The invention, therefore, is to cover all modifications, equivalents, and alternatives falling within the spirit and scope of the invention as defined by the following appended claims.

What is claimed is:

1. A method for refining image data from measured projection data acquired from a computed tomographic scanner comprising:

receiving the measured projection data from the computed tomographic scanner;

reconstructing the measured projection data to generate initial reconstructed image data;

partitioning the initial reconstructed image data into a plurality of regions based on image data quality, to generate partitioned reconstructed image data, wherein the plurality of regions comprise a good image data quality volume and a poor image data quality volume; and refining the image data quality of the partitioned reconstructed image data to generate an improved reconstructed image data.

2. The method of claim 1, wherein the measured projection data comprises cone beam projections.

3. The method of claim 1, wherein reconstructing the measured projection data to generate the initial reconstructed image data is performed using an analytic reconstruction algorithm.

4. The method of claim 3, wherein the analytic reconstruction algorithm comprises a cone beam filtered backprojection reconstruction algorithm to generate the initial reconstructed image data.

5. The method of claim 1, wherein partitioning the initial reconstructed image data into a plurality of regions based on image data quality is based on a reconstruction volume generated by the initial reconstructed image data.

6. The method of claim 1, wherein refining comprises iteratively computing voxel values of the poor image data quality volume.

7. The method of claim 6, further comprising reprojecting the portion of the good image data quality volume to generate good image data quality reprojection data, and reprojecting the poor image data quality volume to generate poor image data quality volume reprojection data.

8. The method of claim 7, further comprising combining the good image data quality reprojection data with the poor image data quality volume reprojection data to generate a combined reprojection data.

9. The method of claim 8, further comprising iteratively reprojecting the poor image data quality volume.

10. The method of claim 8, further comprising comparing the combined reprojection data with the measured projection data to generate a correction term for the poor image data quality volume, wherein the correction term is a measure of the desired image data quality to be attained by the poor image data quality volume.

11. The method of claim 10, further comprising iteratively updating the poor image data quality volume reprojection image data until the correction term attains a pre-determined value.

12. The method of claim 9, wherein iteratively updating the poor image data quality volume comprises using a maximum likelihood transmission iterative reconstruction algorithm.

13. A method of refining image data of an object based on a reconstruction volume generated by initial reconstructed image data of a computed tomographic scanner, comprising:
partitioning the reconstruction volume into a first volume in which radiation paths from a central portion of a radiation beam generated by the computed tomographic scanner intersect radiation paths from diametrically opposed source positions, and a second volume in which radiation paths from an outer portion of a radiation beam generated by the computed tomographic scanner do not intersect radiation paths from diametrically opposed source positions;
partitioning the first volume into a first portion and a second portion;
computing voxel values for voxels of the first volume;
computing voxel values for voxels of the second volume; and
iteratively computing voxel values for voxels of the second volume to generate a refined image data of the object.

14. The method of claim 13, wherein computing voxel values for the voxels of the second volume comprises reprojecting the voxels of the second volume.

15. The method of claim 13, wherein computing voxel values for the voxels of the second volume comprises reprojecting the voxels of the second volume, to generate intersection portion reprojection data.

16. The method of claim 13, wherein the initial reconstructed image data is generated using an analytic reconstruction algorithm.

17. The method of claim 14, wherein reconstructing the voxels of the first volume comprises using an analytic reconstruction algorithm.

18. The method of claim 15, wherein reprojecting the second volume to generate an intersection portion reprojection data comprises using an analytic reconstruction algorithm to form an initial estimate.

19. The method of claim 16, wherein the analytic reconstruction algorithm comprises using a cone beam filtered backprojection reconstruction algorithm.

20. The method of claim 13, wherein iteratively computing voxel values for the voxels of the second volume comprises iteratively correcting the voxels of the second volume, wherein the correction is based upon a comparison between simulated values of projection data and measured projection data.

21. The method of claim 20, wherein iteratively correcting voxel values for the voxels of the second volume comprises using a maximum likelihood transmission iterative reconstruction algorithm.

22. A method for refining image data generated by a computed tomography system comprising:
processing a plurality of electrical signals corresponding to radiation beams generated by the computed tomography system to generate a plurality of projection measurements, wherein the processing comprises performing calculations on the projection measurements to generate reconstruction volume data and wherein the calculations comprise partitioning the reconstruction volume data into a plurality of regions based on image data quality.

23. The method of claim 22, wherein image data for a first volume of the reconstruction volume data is calculated based upon an analytical reconstruction algorithm, and image data for a second volume of the reconstruction volume data is iteratively calculated.

24. The method of claim 23, wherein the analytical reconstruction algorithm comprises a cone beam filtered backprojection reconstruction algorithm.

25. The method of claim 23, wherein the second volume of the reconstruction volume data is iteratively calculated using a maximum likelihood transmission reconstruction algorithm.

26. A computed tomography system for refining image data, the computed tomography system comprising:
an X-ray source configured to project a plurality of X-ray beams through the object;
a detector configured to produce a plurality of electrical signals corresponding to the X-ray beams; and
a processor configured to process the electrical signals to generate a plurality of projection measurements, wherein the processor is configured to perform calculations on the projection measurements to generate reconstruction volume data and wherein the calculations comprise partitioning the reconstruction volume data into a plurality of regions based on image data quality.

27. The system of claim 26, wherein the X-ray source comprises cone beam projections.

28. The system of claim 26, wherein the processor is further configured to compute image data for a first volume of the reconstruction volume data based upon an analytical reconstruction algorithm, and to compute image data for a second volume of the reconstruction volume data iteratively.

29. The system of claim 28, wherein the analytical reconstruction algorithm comprises using a cone beam filtered backprojection reconstruction algorithm.

30. The system of claim 28, wherein the second volume of the reconstruction volume data is iteratively calculated using a maximum likelihood transmission reconstruction algorithm.

31. A computed tomography system for refining image data, the computed tomography system, comprising:
a processor configured to refine the image data based on a reconstruction volume generated from initial reconstructed image data of the computed tomographic scanner, wherein the processor is further configured to partition the reconstruction volume into a first volume in which radiation paths from a first portion of a radiation beam generated by the computed tomographic scanner intersect radiation paths from diametrically opposed source positions, and a second volume in which radiation paths from an outer portion of a radiation beam generated by the computed tomographic scanner do not intersect radiation paths from diametrically opposed source positions, to partition the first volume into first and second portions, to compute voxel values for voxels of the first volume; to compute voxel values for voxels of the second volume; and to iteratively compute voxel values for voxels of the second volume to generate refined image data.

32. The system of claim 31, wherein the processor is configured to generate the initial reconstructed image data, the first volume and the second volume using an analytic reconstruction algorithm.

33. The system of claim 32, wherein the analytic reconstruction algorithm comprises a cone beam filtered back-projection reconstruction algorithm.

34. The system of claim 31, wherein the processor is configured to iteratively compute voxel values for voxels of the second volume based upon an iterative comparison between simulated values of projection data and measured projection data.

35. The system of claim 34, wherein the processor is configured to iteratively compute voxel values for the voxels of the second volume using a maximum likelihood transmission iterative reconstruction algorithm.

36. A computed tomography system for refining image data, the computed tomography system comprising,
  means for partitioning a reconstruction volume into a first volume in which radiation paths from a central portion of a radiation beam generated by the computed tomographic scanner intersect radiation paths from diametrically opposed source positions, and a second volume in which radiation paths from an outer portion of a radiation beam generated by the computed tomographic scanner do not intersect radiation paths from diametrically opposed source positions, wherein the second volume comprises an intersection portion of voxels;
  means for partitioning the first volume into first and second portions;
  means for computing voxel values for voxels of the first volume;
  means for computing voxel values for voxels of the second volume; and
  means for iteratively computing voxel values for voxels of the second volume to generate a refined image data of the object.

37. A system for refining an image data of an object generated by a computed tomography system comprising:
  means for processing a plurality of electrical signals corresponding to radiation beams generated by the computed tomography system to generate a plurality of projection measurements, wherein the processing comprises performing calculations on the projection measurements to generate reconstruction volume data of the object and wherein the calculations comprise partitioning the reconstruction volume data into a plurality of regions based on image data quality.

38. At least one computer-readable medium storing computer instructions for instructing a computer system to refine image data, the computer instructions comprising,
  partitioning a reconstruction volume into a first volume in which radiation paths from a central portion of a radiation beam generated by the computed tomographic scanner intersect radiation paths from diametrically opposed source positions, and a second volume in which radiation paths from an outer portion of a radiation beam generated by the computed tomographic scanner intersect radiation paths from diametrically opposed source positions, wherein the second volume comprises an intersection portion of voxels;
  partitioning the first volume into first and second portions;
  computing voxel values for voxels of the first volume;
  computing voxel values for voxels of the second volume; and
  iteratively computing voxel values for voxels of the second volume to generate a refined image data of the object.

39. At least one computer-readable medium storing computer instructions for instructing a computer system to refine an image data of an object, the computer instructions comprising:
  processing a plurality of electrical signals corresponding to radiation beams generated by the computed tomography system to generate a plurality of projection measurements, wherein the processing comprises performing calculations on the projection measurements to generate reconstruction volume data of the object and wherein the calculations comprise partitioning the reconstruction volume data into a plurality of regions based on image data quality.

* * * * *